United States Patent [19]

Watanabe

[11] Patent Number: 4,922,912
[45] Date of Patent: May 8, 1990

[54] MAP CATHETER

[76] Inventor: Hideto Watanabe, No. 6-21, Nishinagaehonmachi, Toyama-shi, Toyama-ken, Japan

[21] Appl. No.: 252,856

[22] Filed: Oct. 3, 1988

[30] Foreign Application Priority Data

Oct. 21, 1987 [JP] Japan .......................... 62-159998[U]
May 27, 1988 [JP] Japan .......................... 63-070241[U]

[51] Int. Cl.$^5$ .......................... A61B 5/04; A61N 1/05
[52] U.S. Cl. .................................. 128/642; 128/786
[58] Field of Search .................. 128/642, 784–786, 128/419 P

[56] References Cited

U.S. PATENT DOCUMENTS

| | | | |
|---|---|---|---|
| 4,365,639 | 12/1982 | Goldreyer | 128/786 |
| 4,444,195 | 4/1984 | Gold | 128/642 |
| 4,682,603 | 7/1987 | Franz | 128/642 |
| 4,690,155 | 9/1987 | Hess | 128/786 |

OTHER PUBLICATIONS

Gosling, "A Hand-Held Probe . . . ", J. Med. Eng. & Technol. (GB), vol. 3, No. 6, Nov. 1979, p. 299.

Primary Examiner—Lee S. Cohen
Attorney, Agent, or Firm—Hoffmann & Baron

[57] ABSTRACT

An MAP catheter adapted to be directly guided into the cardiac cavity by manual operation of the body thereof through a guide wire inserted into it. It includes a pair of Ag-AgCl lines projecting as a pair of electrodes from the end surface and the peripheral surface in the distal section of the catheter body, respectively, and lead wires connected respectively to the Ag-AgCl lines and extending outwardly beyond the rear end of the catheter body. This catheter body includes, at least in the distal section thereof, an insulating catheter closing section adapted to secure in position the non-projecting sections of the Ag-AgCl lines in a sealed condition.

6 Claims, 2 Drawing Sheets

MAP CATHETER

BACKGROUND OF THE INVENTION

The present invention relates to an MAP (Monophasic Action Potential) catheter adapted to be inserted into the endocardiac cavity for the purpose of measuring the action potential of the myocardiac cells by means of a pair of electrodes. One electrode is situated in the end surface of the catheter body and is brought into contact with the endocardiac surface, and the other on the outer peripheral surface of the catheter body, proximal to the distal end.

This pressure type MAP catheter has recently been developed and is taking the place of the suction type since the latter can injure the myocardium when used for a long period of time and involves a structure and an operation which are rather complicated.

However, its electrodes are formed as masses although they are of the Ag-AgCl line type. As shown in FIG. 6, one electrode 1 of this conventional pressure type MAP catheter is partially projecting from the tip of the catheter body 2, and the other electrode 3 is exposed through a hole made in a peripheral surface 2a in the tip section, both electrodes being secured in position by means of cement 4 ("THE AMERICAN JOURNAL OF CARDIOLOGY", vol. 51, June 1983, on page 1631).

This structure requires Ag which is an expensive material in an amount corresponding to the spherical configuration of the electrodes. Further, there is the danger of the endocardium being injured since the cement section 4 is directly pushed by a guide wire 5 through a sheath 6. Besides, the hole 2b provided in the peripheral surface 2a in the distal section is liable to be clogged up with foreign matter, resulting in the electrode being in a poor contact with blood.

SUMMARY OF THE INVENTION

Accordingly, it is an object of the present invention to provide a MAP catheter of the type described above which requires a smaller amount of Ag and which offers a high measurement reliability.

Another object of this invention is to provide an MAP catheter of the type described above which ensures a high safety.

The present invention which aims at attaining these objects is based upon the recognition that if the conventional mass-like configuration of the electrode can enlarge the area in which the electrodes and the endocardium are in contact with each other, the increased polarization voltage leads to an apparently augmented contact resistance. In accordance with this invention, there is provided a MAP catheter having a pair of Ag-AgCl lines projecting as a pair of electrodes from the front end surface and the peripheral surface in the distal section, of the catheter body, respectively. A catheter closing section adapted to secure the non-projecting sections of the Ag-AgCl lines in position in a sealed condition, is provided in the distal section of the catheter body. Connected to the Ag-AgCl lines are lead wires which extend beyond the rear end of the catheter body. The catheter body may be operated by means of a guide wire inserted into it through the intermediary of an elastic body provided between the catheter closing section and the elastic body, or it may be directly guided by hand at the rear end thereof.

In accordance with this invention, the amount of Ag used can be reduced and the myocardiac action potential can be measured with higher sensitivity and fidelity with reduced generation of polarization voltage. Since the distal electrode is formed as a projecting needle which is pressed against the object of detection, it can be positively brought into contact with the endocardiac surface. The side electrode is also formed as a projecting needle, so that there is no danger of foreign matter adhering to the electrode surface. This allows the measurement to be performed with high reliability for a longer period of time.

Further, by providing an elastic body behind the catheter closing section, such an accident as injuring of the endocardium by any excessive pressure exerted to the catheter body can be positively avoided when manipulating the catheter through the guide wire or directly by hand. A spherical configuration of the distal section of the needle-like electrodes enables them to be guided and brought into contact with the endocardium more smoothly and positively. This also enhances the safety of the instrument. By adding a pair of pacing electrodes to the peripheral surface of the catheter distal section, MAP measurement can be conducted with high accuracy in a pacing condition.

With an MAP catheter of such a practical value, it is hoped, clinical application of catheters to cardiac diseases will be more actively practised.

DESCRIPTION OF THE PREFERRED EMBODIMENTS

Figure 1:
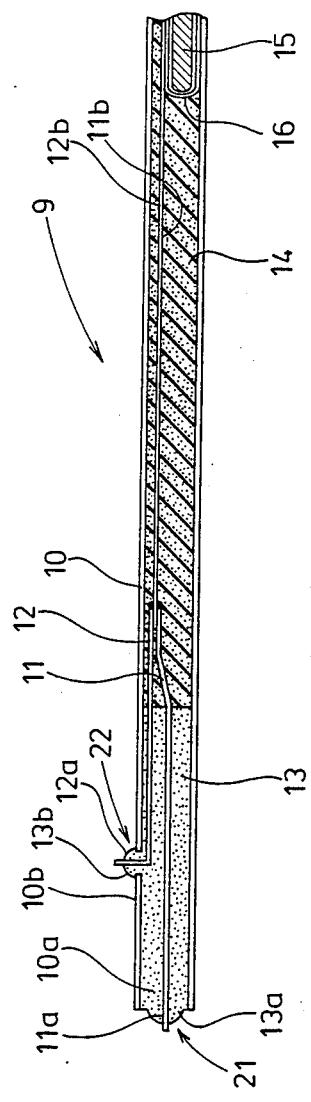
FIG. 1 is a sectional view showing the essential parts of an MAP catheter in accordance with the first embodiment of the present invention.
Figure 2:
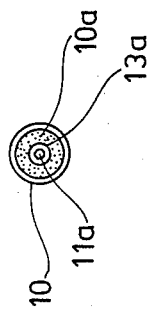
FIG. 2 is a front view of the catheter distal section of this embodiment.

As shown in FIG. 1, a MAP catheter 9 in accordance with the first embodiment of the present invention has a catheter body 10 having a diameter of, for example, 2 mm and consisting of a tube made of a plastic material such as vinyl chloride or polyurethane. An Ag-AgCl line 11 consisting of an Ag line plated with AgCl and having a diameter of, for example, 0.3 mm is projecting ca. 0.5 mm from the central position of the front end surface 10a (FIG. 2) as the first electrode. An Ag-AgCl line 12 is also projecting ca. 0.5 mm from a hole provided in the peripheral surface 10b which hole is, for example, 5 mm proximal to the end surface 10a, in a direction perpendicular to that of the Ag-AgCl line 11, as the second electrode. The distal section of the catheter body 10 is filled with epoxy cement 13 to secure the Ag-AgCl lines 11 and 12 in position and to form a catheter closing section. The sections of the Ag-AgCl lines 11 and 12 which are not projecting outwardly are completely sealed in to prevent blood from intruding. The projecting sections 11a and 12a of the Ag-AgCl lines 11 and 12 are surrounded by an approximately semispherical epoxy cement portions 13a and 13b, respectively, thus forming a pair of electrodes 21 and 22.

The Ag-AgCl lines 11 and 12 extend from the catheter section which is filled with the epoxy cement 13 along the inner wall of the catheter 10. On the way, they are connected to respective wires 11b and 12b to be led out from the rear end of the catheter body 10. FIG. 1 only shows the front essential portion of the catheter body 10 which has a length of ca. 1 to 1.5 m. An elastic material such as silicone rubber 14 with an elastic coefficient of Shore A 300 is provided behind the section which is filled with epoxy cement and extends over a length of 20 mm, for example. A sheath 16 for inserting the guide wire is inserted from behind and extends up to this silicone rubber section 14.

Figure 6:
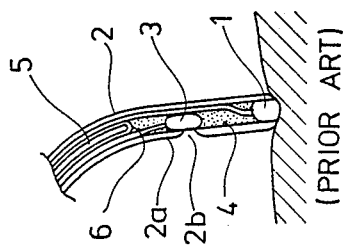
FIG. 6 is a sectional view showing the essential parts of a conventional MAP catheter.

The MAP catheter 9 thus constructed is guided within a blood vessel by the guide wire 15 and inserted into the cardiac cavity. Particularly, the semispherical configuration of the portion 13a surrounding the electrode 21 enables the slightly exposed portion of the projecting section 11a to be positively guided over and brought into contact with the endocardium. Since the electrode 22 is also provided with a semispherical surrounding portion 13b, the catheter 9 can be smoothly guided into the cardiac cavity without suffering any damage. When set in position inside the cardiac cavity, the exposed portion of the projecting section 12a of the side electrode 22 is protruding beyond the peripheral surface of the catheter body, so that, unlike the electrode 3 in FIG. 6, there is no danger of foreign matter adhering thereto. Accordingly, the electrode is positively brought into contact with the blood. Since the silicone rubber section 14 is provided between the guide wire 16 and the epoxy cement section 13, the pressure exerted by the guide wire 15 through the sheath 16 is softened, which ensures operational safety.

The action potential of the measured regions transmitted through the lead wires 11b and 12b extending from the rear end (not shown) of the catheter body 10 is amplified by an output apparatus. It is then recorded on recording paper, and, as needed, monitored on a cathode-ray tube. The measurement can be performed at one or several positions for a long period of time with safety. Since the polarization voltage can be restrained to a minimum, the measurement can be conducted not only with high sensitivity but with a faithful MAP waveform.

Figure 3:
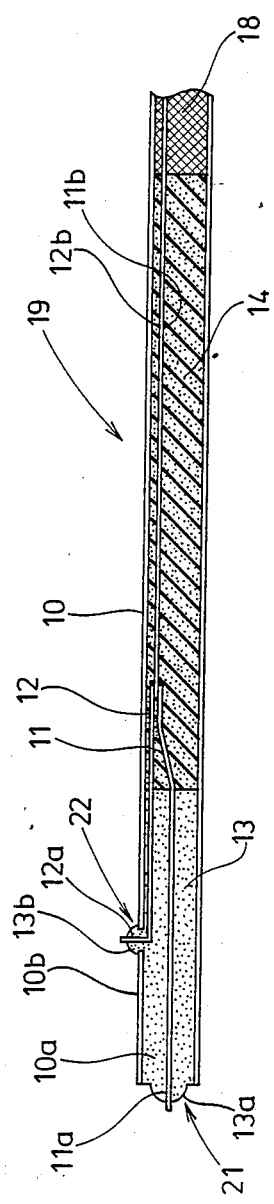
FIG. 3 is a sectional view showing the essential parts of an MAP catheter in accordance with the second embodiment of the present invention.

FIG. 3 shows a second embodiment of this invention in which no guide wire is used. In the drawing, the parts which are identical with those in FIG. 1 have the same reference characters.

In this embodiment, the Ag-AgCl lines 11 and 12 likewise extend from the section which is filled with epoxy cement 13 along the inner wall of the catheter body 10. They are connected to the wires 11b and 12b and extend through a WOVEN DACRON section 18 to be led out from the rear end of the catheter body 10. Silicone rubber 14 with the above elastic coefficient, for example, is provided in the section extending 30 mm, for example, between the epoxy cement section 13 and the WOVEN DACRON section 18. The catheter body 10 into which the WOVEN DACRON is thus inserted is advantageous in that it has flexibility and that the pressure and torque generated through direct manipulation at the rear end are positively transmitted to the front end.

When performing measurement, the MAP catheter 19 is guided within the blood vessel and inserted into the cardiac cavity by manipulating it at its rear end. The silicone rubber 14 provided between the WOVEN DACRON 18 and the epoxy cement 13 serves to soften any impact exerted by excessive pressure during operation, thereby ensuring operational safety.

Figure 4:
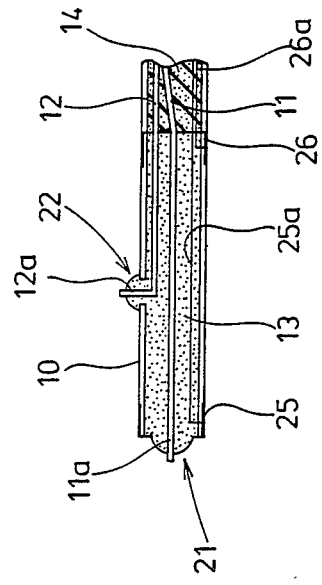
FIG. 4 is a sectional view showing the essential parts of an MAP catheter in accordance with the third embodiment of the present invention.

FIG. 4 shows a third embodiment of the present invention. In the drawing, the components which are identical with those in FIGS. 1 and 3 have the same reference characters.

In this embodiment, annular pacing electrodes 25 and 26 made of stainless steel or platinum are embedded in the distal section of the catheter 10 in such a manner that they are in a plane with the surface of the catheter 10. For this purpose, the corresponding portions of the catheter body 10 are cut away. Inside, they are connected to lead wires 25a and 26a which extend outwardly from the rear end of the catheter body 10 so that they may be connected to a pacing apparatus, thus forming a MAP catheter with pacing electrodes. This structure makes it possible to conduct MAP measurement while performing pacing and sensing with a single catheter, thereby enabling a local myocardiac action corresponding to a change in heart rate to be monitored closely. In addition, due to the integrated structure, the annular electrodes 25 and 26 can be provided in the vicinity of the electrodes 21 and 22, which results in higher accuracy.

Figure 5B:
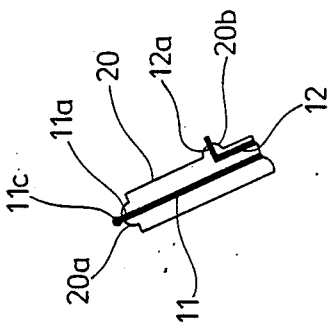
FIGS. 5a and 5b shows an MAP catheter in accordance with the fourth embodiment of the present invention.
Figure 5A:
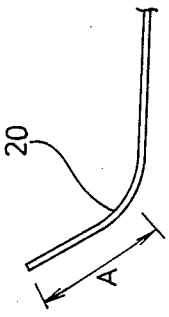

FIGS. 5a and 5b show a fourth embodiment of the present invention. As shown in FIG. 5a, which is a schematic side view of this embodiment, the catheter body 20 is previously curved over a range A extending ca. 50 mm from the distal end. This catheter body 20, including the semispherical surrounding portions 20a and 20b, is formed in one piece from the front to the rear end as a solid body of the same plastic material in which the electrodes and lead wires are embedded. Accordingly, the guiding operation is performed without using a guide wire. Furthermore, as shown in FIG. 5b, which is an enlarged sectional view of this embodiment, the exposed portion 11c of the projecting section 11a of the Ag-AgCl line which protrudes beyond the surrounding portion 20a is rounded so as to enhance safety.

In the above described embodiments, the semispherical surrounding portions 13a and 13b of the Ag-AgCl lines may be dispensed with in some instances. The desired results can be obtained without them.

Further, the front end surface of the catheter body may be formed as a closed section which is in one piece with the catheter body proper, the non-projecting section of the Ag-AgCl line 12 being embedded in the tube surface of the catheter body 10. The semispherical surrounding portions may then be formed in one piece with the distal end section positioning the Ag-AgCl lines and the elastic body. For the elastic body provided behind the catheter closing section, other materials may be employed. The annular configuration of the pacing electrodes ensures positive contact with the endocardium. However, the electrodes may, in some cases, have a pointed configuration.

What is claimed is:

1. A MAP catheter comprising:
    a catheter body including a distal section and a rear section, said distal section having an end surface and a peripheral surface;
    a pair of Ag-AgCl lines projecting as a pair of needle-like electrodes from said end surface and said peripheral surface in said distal section of said catheter body, respectively, said catheter body including at least in said distal section thereof, an insulating catheter closing section securing in position and in a sealed condition portions of said Ag-AgCl lines and disposed within said catheter body, a pair of lead wires connected respectively to said Ag-AgCl lines and extending outwardly beyond the rear section of said catheter body.

2. The MAP catheter as claimed in claim 1, wherein said catheter closing section occupies only the distal section of the catheter, and an elastic body is provided behind said catheter closing section and before said rear section of said catheter body, and a guide wire is inserted at a position behind said elastic body and before said rear section.

3. The MAP catheter as claimed in claim 1, wherein said catheter closing section occupies only the distal section of said catheter body, and an elastic body is provided behind said catheter closing section and before said rear section of said catheter body, and wherein a flexible material is inserted at a position behind said elastic body and before said rear section so as to render said catheter body directly guidable at said rear section thereof.

4. The MAP catheter as claimed in claim 1, wherein approximately semispherical surrounding portions are formed around said needle-like electrodes projecting from said end surface and said peripheral surface of said distal section of said catheter body.

5. The MAP catheter as claimed in claim 1 which further comprises a pair of pacing electrodes provided to said peripheral surface of said distal section of said catheter body, and a pair of lead wires connected to said pair of pacing electrodes respectively, and extending outwardly beyond said rear section of said catheter body.

6. The MAP catheter as claimed in claim 1, wherein said distal section of the catheter body has a predetermined curvature.

* * * * *